United States Patent [19]

Brayer et al.

[11] Patent Number: 5,310,746

[45] Date of Patent: May 10, 1994

[54] ALPHA-METHYLENE-6-STYRYL-ACRYLIC ACID DERIVATIVES

[75] Inventors: Jean-Louis Brayer, Nanteuil Le Haudoin; Jean-Pierre Demoute, Neuilly Plaisance; Yannick Le Stanc, Pontault Combault; Nicole Reinier, Marseille, all of France

[73] Assignee: Roussel Uclaf, France

[21] Appl. No.: 981,071

[22] Filed: Nov. 24, 1992

[30] Foreign Application Priority Data

Nov. 26, 1991 [FR] France .................. 91 14556

[51] Int. Cl.$^5$ .................. C07C 69/618; C07D 277/30; A01N 37/10; A01N 43/78
[52] U.S. Cl. ..................... 514/361; 514/342; 514/365; 514/544; 546/280; 548/131; 548/204; 560/60
[58] Field of Search .................. 560/60; 548/204, 131; 546/280; 514/361, 365, 342, 544

[56] References Cited

U.S. PATENT DOCUMENTS

| | | | |
|---|---|---|---|
| 5,166,167 | 11/1992 | Brager | 514/365 |
| 5,210,093 | 5/1993 | Brager | 514/365 |

Primary Examiner—Robert Gerstl
Attorney, Agent, or Firm—Bierman and Muserlian

[57] ABSTRACT

All possible stereoisomer forms and mixtures of a compound of the formula

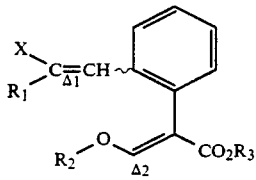

wherein X is a halogen, $R_2$ and $R_3$ are individually selected from the group consisting of alkyl and cycloalkyl of up to 8 carbon atoms optionally substituted with at least one halogen, $R_1$ is selected from the group consisting of alkyl, alkenyl, alkynyl and cycloalkyl of up to 12 carbon atoms optionally substituted with at least one halogen, aryl and heteroaryl of 5 to 6 ring members optionally substituted with at least one member of the group consisting of halogen, alkyl, alkenyl, alkynyl and cycloalkyl of up to 8 carbon atoms optionally substituted with at least one member of the group consisting of $-NO_2$, $-NH_2$, $-CN$, $-OR'$, $-SR''$, $-SOR''$, $-SO_2R''$, $-NR'''_2$, $-Ar$, $OAr_1$ and $SAr_2$, $R'$, $R''$ and $R'''$ are individually selected from the group consisting of alkyl, alkenyl, alkynyl and cycloalkyl of up to 12 carbon atoms optionally substituted by at least one halogen, Ar, $Ar_1$ and $Ar_2$ are aryl or heteroaryl of up to 14 carbon atoms optionally substituted with at least one member of the group consisting of halogen and alkyl, alkenyl, alkynyl and cycloalkyl of up to 8 carbon atoms optionally substituted by at least one member of the group consisting of halogen, $-NO_2$, $-NH_2$, $-CN$, $-OR'$, $-SR''$, $-SOR''$, $-SO_2R''$ and $-NR'''_2$ and $R'$, $R''$ and $R'''$ have the above definitions and their preparations and novel intermediates useful as pesticides.

16 Claims, No Drawings 5,310,746

ALPHA-METHYLENE-6-STYRYL-ACRYLIC ACID DERIVATIVES

STATE OF THE ART

Related prior art includes European patent applications 0,178,826 and No. 0,402,246 and U.S. Pat. No. 4,822,908.

OBJECTS OF THE INVENTION

It is an object of the invention to provide the novel compounds of formula I and a process and intermediates for their preparation.

It is another object of the invention to provide novel pesticidal compositions and a method of combatting pests.

These and other objects and advantages of the invention will become obvious from the following detailed description.

THE INVENTION

The novel α-methylene-6-styryl-phenyl-acrylic compounds of the invention are all possible stereoisomer forms and mixtures of a compound of the formula

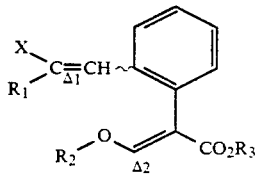

wherein X is a halogen, $R_2$ and $R_3$ are individually selected from the group consisting of alkyl and cycloalkyl of up to 8 carbon atoms optionally substituted with at least one halogen, $R_1$ is selected from the group consisting of alkyl, alkenyl, alkynyl and cycloalkyl of up to 12 carbon atoms optionally substituted with at least one halogen, aryl and heteroaryl of 5 to 6 ring members optionally substituted with at least one member of the group consisting of halogen, alkyl, alkenyl, alkynyl and cycloalkyl of up to 8 carbon atoms optionally substituted with at least one member of the group consisting of —NO$_2$, —NH$_2$, —CN, —OR', —SR", —SOR", —SO$_2$R", —NR'"$_2$, —AR, —OAr$_1$ and —SAr$_2$, R', R" and R'" are individually selected from the group consisting of alkyl, alkenyl, alkynyl and cycloalkyl of up to 12 carbon atoms optionally substituted by at least one halogen, Ar, Ar$_1$ and Ar$_2$ are aryl or heteroaryl of up to 14 carbon atoms option-ally substituted with at least one member of the group consisting of halogen and alkyl, alkenyl, alkynyl and cycloalkyl of up to 8 carbon atoms optionally substituted by at least one member of the group consisting of halogen, —NO$_2$, —NH$_2$, —CN, —OR', —SR", —SOR", —SO$_2$R" and —NR'"$_2$ and R, R" and R'" have the above definitions.

The geometry of the double bonds $\Delta_1$ and $\Delta_2$ is E or Z or a mixture of E and Z geometry. Halogen is preferably fluorine, chlorine or bromine.

In the definition of the different substituents, alkyl preferably is methyl, ethyl, propyl, isopropyl, butyl, isobutyl, secbutyl or tert-butyl, alkenyl preferably is vinyl, allyl or 1,1-dimethylallyl, alkynyl preferably is ethynyl or propynyl.

Aryl preferably is phenyl or naphthyl and heteroaryl preferably is pyridyl, pyrimidyl, pyridazinyl, oxazolyl, thiazolyl, isoxazolyl, isothiazolyl, (1,3,4)-oxadiazolyl, (1,2,4)-oxadiazolyl, thiadiazolyl or triazolyl. The alkyl substituted by at least one halogen preferably is —CF$_3$. Among the preferred compounds of formula I are those wherein the double bond $\Delta_2$ is of E geometry, those wherein $R_2$ is methyl, those wherein $R_3$ is methyl, those wherein X is fluorine, those wherein $R_1$ is phenyl optionally substituted by at least one member of the group consisting of halogen and —CF$_3$, those wherein $R_1$ is thiazolyl optionally substituted by at least one member of the group indicated above for example thiazolyl substituted by at least one member of the group consisting of halogen and phenyl optionally substituted by at least one member of the group consisting of halogen, —CF$_3$ and —OCF$_3$, those wherein $R_1$ is oxadiazolyl optionally substituted by at least one member of the groups indicated above, for example oxadiazolyl substituted by phenyl optionally substituted by at least one member of the group consisting of halogen and —CF$_3$ and —OCF$_3$.

Specific preferred compounds of formula I are those of Examples 1, 4, 5, 7, 18, 20, 25, 26 and 30.

The novel process of the invention for the preparation of a compound of formula I comprises reacting a compound of the formula

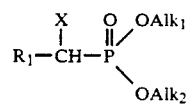

wherein $R_1$ and X have the above definitions and Alk$_1$ and Alk$_2$ are individually alkyl of 1 to 8 carbon atoms with a compound of the formula

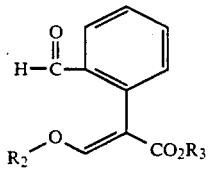

wherein $R_2$ and $R_3$ have the above definition in the presence of a basic agent to obtain the corresponding compound of formula I which optionally is separated into its individual isomers and optionally converting one isomer into the other.

The basic agent is a strong base such as sodium hydride, alkali metal and alkaline earth metal alcoholates such as potassium tert.-butylate or sodium tert.-butylate, alkali metal amides or an organolithium compound.

The compounds of formula I wherein $R_1$ is a monosubstituted aryl or heteroaryl may be reacted with a reagent capable of introducing another substituent. It can be halogenated by a bromination in an organic solvent such as carbon tetrachloride for example. The compounds of formula I with an aryl or heteroaryl substituted with a halogen can be subjected to an alkenylation, alkynylation, arylation or heteroarylation by a catalyzed organometallic or palladium coupling reaction.

The isomer separation may be effected by standard known methods. The isomerization of fluorinated double bonds can be achieved with a catalytic amount of bromine in the presence of luminous radiation.

The compounds of formulae II and III are novel. The compounds of formula II can be prepared by the following reaction scheme

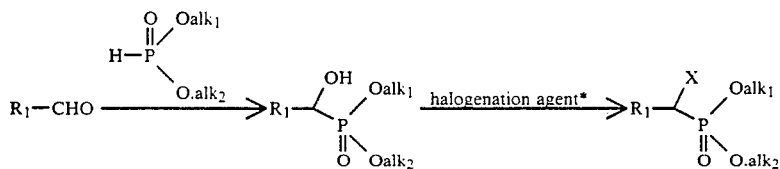

OR

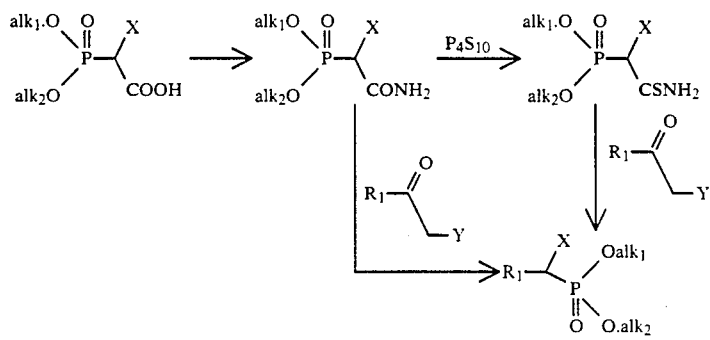

*The halogenation agent can be $SOCl_2$, $PCl_3$, $POCl_3$, $P(C_6H_5)_3$—$CCl_4$ or diethylaminosulfide trifluoride (DAST).

The compounds of formula III can be prepared by the following reaction schemes

1st METHOD

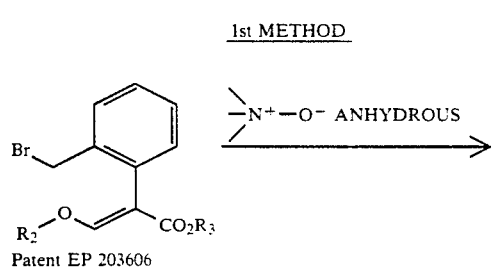

Patent EP 203606

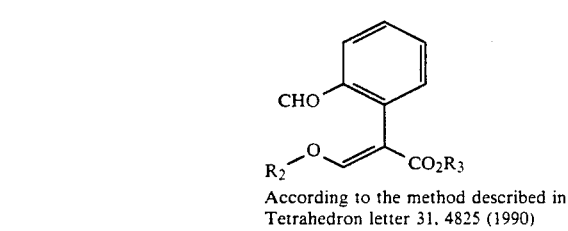

According to the method described in Tetrahedron letter 31, 4825 (1990)

2nd METHOD

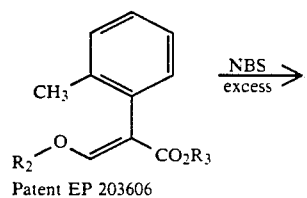

Patent EP 203606

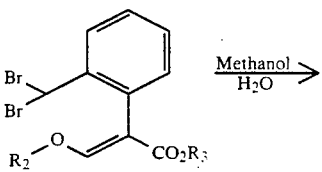

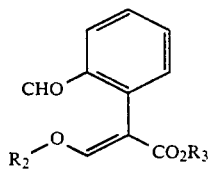

The pesticidal compositions of the invention are comprised of a pesticidally effective amount of at least one compound of formula I and an inert carrier. The compositions are useful as insecticides, acaricides and nematocides. Preferred are compositions containing at least one compound of Examples 1, 4, 5, 7, 18, 20, 25, 26 and 30.

The compositions can be used particularly to combat insects in the agricultural domain, to combat for example fleas, lepidoptera and coleoptera larvae. They are used at doses comprised between 10 g and 1000 g of active ingredient per hectare.

The compositions can also be used to combat insects in premises, in particular to combat flies, mosquitoes and cockroaches and can also be used to combat parasitic acaridae of vegetation as well as to combat parasitic nematodes of vegetation.

The compositions can be used to combat parasitic acaridae of animals, such as ticks and notably ticks of the Boophilus species, those of the Hyalomnia species, those of the Amblyomnia species and those of the Rhipicephalus species or to combat all sorts of mites and notably the sarcoptic mite, the psoroptic mite and the chorioptic mite.

Therefore the compositions are intended to combat parasites of warm-blooded animals, parasites of premises and vegetation. Preferred are insecticide compositions containing as active ingredient at least one of the products defined above.

The compositions of the invention are prepared by the usual processes of the agrochemical industry or the veterinary industry or the animal-feed products industry.

The compositions can be in the form of powders, granules, suspensions, emulsions, solutions, aerosol solutions, combustible strips, baits or other preparations usually employed for the use of this type of compound.

In addition to the active ingredient, these compositions contain generally a vehicale and/or a non-ionic surfactant to ensure a uniform dispersion of the components of the mixture. The vehicle can be a liquid such as water, alcohol, hydrocarbons or other organic solvents, a mineral, animal or vegetable oil, a powder such as talc, clays, silicates, kieselguhr or a combustible solid.

The insecticide compositions according to the invention contain preferably 0.005% to 10% by weight of active ingredient.

According to an advantageous operating method, for use in premises, the compositions may be used in the form of fumigant compositions and can then be advantageously composed of, for the nonactive part, a combustible insecticide coil, or an incombustible fibrous substrate. In the latter case, the fumigant obtained after incorporation of the active ingredient is placed on a heating apparatus such as an electric mosquito destroyer.

When an insecticide coil is used, the inert support can be, for example, composed of Pyrethrum marc, Tabu powder (or Machilus Thumbergii leaf powder), Pyrethrum stem powder, cedar leaf powder, sawdust (such as pine sawdust), starch and coconut shell powder. The dose of active ingredient can then be, for example, 0.03 to 1% by weight. In the case of an incombustible fibrous support, the dose of active ingredient can then be, for example, 0.03 to 95% by weight.

The compositions of the invention for use in premises can also be obtained by preparing a sprayable oil based on the active ingredient, this oil soaking a lamp wick and then being set alight. The concentration of active ingredient incorporated into the oil is preferably 0.03 to 95% by weight.

The acaricide compositions and the nematicide compositions contain as the active ingredient at least one of the products of formula I as defined above.

The insecticide compositions of the invention, as well as the acaricide and nematocide compositions can optionally have other pesticide agents added to them. The acaricide and nematocide compositions can be presented in the form of powders, granules, suspensions, emulsions or solutions.

For acaricide use, wettable powders are preferably used for foliar spraying contain 1 to 80% of active ingredient or liquids for foliar spraying contain 1 to 500 g/1 of active ingredient. Powders for foliar dusting contain 0.05% to 3% of active ingredient. For nematocide use, liquids for soil treatment containing 300 to 500 g/1 of active ingredient are preferably used.

The acaricide and nematocide compounds of to the invention are used preferably at doses comprised between 1 and 100 g of active ingredient per hectare. The acaricide compositions intended to combat the parasitic acaridae of warm-blooded animals, particularly against ticks and mites, contain as active ingredient at least one of the products of formula I.

The novel method of combatting pests, especially insects, comprises contacting the pests with a pesticidally effective amount of at least one compound of formula I.

In the following examples, there are described several preferred embodiments to illustrate the invention. However, it should be understood that the invention is not intended to be limited to the specific embodiments.

EXAMPLE 1

Methyl 2-[2-(4-bromo-3-trifluoromethyl-phenyl)-2-fluoroethenyl -α-(methoxymethylene) benzene acetate Z,E isomer and E,E isomer A solution of 1.3 g of potassium tert.-butylate and 10 ml of tetrahydrofuran was introduced at −60° C. into a solution of 4.3 g of diethyl [4-bromo-3-trifluoromethyl-phenyl-fluoromethyl]-phosphonate (Preparation 2) and 20 ml of tetrahydrofuran. The reaction mixture was stirred for 15 minutes at −60° C. and a solution of 2.4 g of methyl 2-formyl-α-(methoxymethylene) benzene acetate (Preparation 1) and 15 ml of tetrahydrofuran were introduced without allowing the temperature to exceed −50° C. The temperature of the reaction mixture was allowed to rise to approx. 20° to 25° C. and the mixture was stirred at 20° to 25° C. for 1 hour. The mixture was poured into a mixture of water +1N hydrochloric acid (100 ml) and isopropyl ether 200 ml. After decanting and extracting with isopropyl ether, the extracts were dried and chromatographed on silica eluting with a hexane - ethyl acetate (8–2) mixture to obtain the desired product melting at 115.5° C. Z,E isomer and 103.1° C. E,E isomer.

EXAMPLE 2

Methyl 2-[2-[2-[3.4-dichlorophenyl)-4-thiazolyl]-2-fluoroethenyl] -α-(methoxymethylene) benzene acetate Z,E isomer and E,E isomer A solution of 0.7 g of potassium tert.-butylate and 6 ml of tetrahydrofuran was introduced at 0° C. into a mixture of 1.33 g of the product of Preparation 1, 2.4 g of the product of Preparation 3, diethyl 2-(3,4-dichlorophenyl-4-thiazolyl)-fluoromethyl phosphonate, and 10 ml of tetrahydrofuran. The reaction mixture was held at 0°+5° C. for one hour and was poured into a mixture of 100 ml of 1N hydrochloric acid and 100 ml of methylene chloride. After decanting, the aqueous phase was extracted twice with 100 ml of methylene chloride, followed by drying and bringing to dryness. The residue was chromatographed on silica eluting with a hexane - isopropyl ether (7–3) mixture to obtain 0.6 g of Z,E isomer melting at 153.2° C., and 0.6 g of E,E isomer melting at 112.1° C.

EXAMPLE 3

Methyl 2-[2-[2-(2,4-dichlorophenyl)-4-thiazolyl]-2-fluoro-ethenyl] -α-(methoxymethylene) benzene acetate Z,E isomer and Z,E and E,E mixture A solution of 0.57 g of potassium tert.-butylate and 5 ml of tetrahydrofuran was introduced at 0°+5° C. into a solution of 1.06 g of the product of Preparation 1 and 1.9 g of diethyl 2-(2,4-dichlorophenyl-4-thiazolyl)- fluoromethyl phosphonate of Preparation 3 starting with 2-[2-(2,4-dichlorophenyl)-4-formyl thiazole and 10 ml of tetrahydrofuran. The reaction mixture was stirred for 3 hours at 0°+5° C. and was poured into a mixture of 1N hydrochloric acid and 100 ml of isopropyl ether. After decanting and extracting with isopropyl ether, the extracts were dried over sodium sulfate and evaporated to dryness. The residue was chromatographed on silica eluting with a hexane - isopropyl ether (7–3) mixture to obtain 0.9 g of product which was chromatographed on silica eluting with a hexane - isopropyl ether (8–2) mixture to obtain 0.11 g of the desired Z,E product and 0.57 g of E,E and Z,E mixture 75 to 25 melting at 123.8° C.

EXAMPLE 4

Methyl 2-[2-fluoro-2-[4-thiazolyl-2-(4-trifluoromethoxy)-phenyl] ethenyl]-α-(methoxymethylene) benzene acetate, Z,E isomer and E,E isomer A solution of 0.53 g of potassium tert.-butylate and 2.4 ml of tetrahydrofuran was added at 0° C. to a mixture of 0.92 mg of methyl 2-formyl-α-(methoxymethylene) benzene acetate (Preparation 1), 1.8 g of diethyl-[fluoro-[4-(4-trifluoromethoxy-phenyl)-2-thiazolyl]methyl]-phosphonate (Preparation 4) and 3 ml of tetrahydrofuran. The reaction mixture was stirred for 16 hours and acidification to pH 4 was carried out by the addition of 1N hydrochloric acid, followed by extraction with methylene chloride. The extracts were washed with water and dried. The solvent was evaporated to obtain 2.3 g of product which was chromatographed on silica. Elution with a hexane - ethyl acetate (85–15) mixture yielded 0.2 g of the Z,E isomer product melting to 137.9° C. and 0.44 g of the E,E product melting at 99.5° C.

EXAMPLE 5

Methyl 2-[2-fluoro-2-(4-phenyl-2-thiazolyl)-ethenyl]-α-(methoxymethylene) benzene acetate, (Z+E), E mixture 233 mg of sodium hydride at 50% in oil were added to a solution of 1.07 g of methyl 2-formyl- α-(methoxymethylene) benzene acetate (Preparation 1), 1.6 g of [diethyl-fluoro-4-phenyl-2thiazolyl]-methyl]-phosphonate (Preparation 5) and 10 ml of tetrahydrofuran. The reaction mixture was stirred for 16 hours and then was poured into an aqueous solution of hydrochloric acid. After extracting with methylene chloride and drying, the solvent was evaporated to obtain 2.27 g of product which was chromatographed on silica. Elution with a hexane - ethyl acetate (80–20) mixture yielded 1.46 g of an oil which was processed with pentane to obtain 1.07 g of the desired product melting at 94° C.

EXAMPLE 6

Methyl α-(methoxymethylene)-2-[2-fluoro-2-[4-(1-methylethyl)-2thiazolyl]-ethenyl] benzene acetate, Z,E isomer and E,E isomer A solution of 1.45 g of potassium tert.-butylate and 6 ml of tetrahydrofuran was added dropwise to a mixture of 2.83 g of methyl 2-formyl-α-(methoxymethylene) benzene acetate, 3.8 g of diethyl fluoro [4-isopropyl-2-thiazolyl]-methyl]-phosphonate (Preparation 6) and 15 ml of tetrahydrofuran and the reaction mixture was stirred overnight. The pH was adjusted to 4, followed by extracting with methylene chloride, washing and drying. The solvent was eliminated to obtain 5.23 g of product which was chromatographed on silica. Elution with a hexane - ethyl acetate (85–15) mixture yielded 0.34 g of Z,E isomer melting at 104.3° C. and 1 g of E,E isomer.

EXAMPLE 7

Methyl 2-[2-(4-(3,4-dichlorophenyl)-2-thiazolyl]-2-fluoro ethenyl -α-(methoxymethylene) benzene acetate Z,E isomer and E,E isomer 326 mg of sodium hydride at 50% in oil were added to a solution of 1.5 g of methyl 2-formyl-α-(methoxymethylene) benzene acetate (Preparation 1), 2.7 g of diethyl [4-(3,4-dichlorophenyl) -2-thiazolyl]-fluoromethyl]-phosphonate (Preparation 7) and 10 ml of tetrahydrofuran and the reaction mixture was stirred overnight. It was poured into water and was extracted with methylene chloride. The organic phases were dried and the solvent was evaporated to obtain 3.66 g of product which was chromatographed on silica. Elution with a hexane - ethyl acetate (85–15) mixture yielded 0.22 g of Z,E isomer melting at 192.3° C. and 1.52 g of E,E isomer melting at 115.6° C.

Using the procedure of the above examples, methyl-2-formyl -α-(methoxymethylene) benzene acetate and the appropriate phosphonate were reacted to obtain the following products.

EXAMPLE 8

Methyl 2-[2-fluoro-2-[2-trifluoromethyl-4-thiazolyl-]ethenyl]-(methoxymethylene benzene acetate - (Z,E) isomer and (E,E) isomer with the Z,E isomer melting at 143° C.

EXAMPLE 9

Methyl 2-[2-[4-[(1,1'-biphenyl)-4-yl]-2-thiazolyl]-2-fluoro ethenyl]-α-(methoxymethylene) benzene acetate - with the Z,E isomer melting at 121.6° C. and the E,E isomer melting at 139.5° C.

EXAMPLE 10

Methyl 2-[2-[4-(4-chlorophenyl)-2-thiazolyl]-2-fluoroethenyl]-α-(methoxymethylene) benzene acetate with the Z,E isomer melting at 137.2° C. and the E,E isomer melting at 116.5° C.

EXAMPLE 11

Methyl 2-[2-[4-(4-bromophenyl)-2-thiazolyl]-2-fluoroethenyl]-α-(methoxymethylene) benzene acetate with the Z,E isomer melting at 145.8° C. and the E,E isomer melting at 132.5° C.

EXAMPLE 12

Methyl 2-[2-fluoro-2-[4-(trifluoromethyl)-2-thiazolyl] ethenyl-α-(methoxymethylene) benzene acetate with the Z,E isomer melting at 109° C. and also the E,E isomer.

EXAMPLE 13

Methyl 2-[[2'-ethyl-(2,4'-bithiazole)-4-yl]-2-fluoroethenyl]-α-(methoxymethylene) benzene acetate with a mixture of Z,E isomers (80–20) melting at 83.5° C.

EXAMPLE 14

Methyl 2-[2-fluoro-2-[2-pyridinyl-4-thiazolylethenyl]-α-(methoxymethylene) benzene acetate with the Z,E isomer melting at 146° C. and the E,E isomer melting at 101° C.

EXAMPLE 15

Methyl 2-[2-fluoro-2-[3-[4-(trifluoromethoxy)-phenyl]1,2,4-oxadiazol-5-yl]] ethenyl]-α-(methoxymethylene) benzene acetate with the E,E isomer melting at 103.6° C.

EXAMPLE 16

Methyl 2-[2-fluoro-2-[3-(trifluoromethyl)-phenyl]ethenyl]-α-(methoxymethylene) benzene acetate with the Z,E isomer melting at 90° C. and the E,E isomer melting at 61.5° C.

EXAMPLE 17

Methyl 2-[2-fluoro-2-[4-(4-nitrophenyl)-2-thiazolyl]ethenyl]-α-(methoxymethylene) benzene acetate with the mixture of (Z,E), E) isomers melting at 79° C.

EXAMPLE 18

Methyl 2-[2-[4-(4-fluorophenyl)-2-thiazolyl]-2-fluoroethenyl]- α-(methoxymethylene) benzene acetate with the Z,E isomer melting at 135.8° C. and the E,E isomer melting at 99.8° C.

EXAMPLE 19

Methyl α-(methoxymethylene)-2-[2-(3-bromophenyl)-2-fluoroethenyl benzene acetate with the Z,E isomer melting at 129° C. and the E,E isomer melting at 94° C.

EXAMPLE 20

Methyl 2-[2-5-bromo-4-(3,4-dichlorophenyl)-2-thiazolyl]-2-fluoroethenyl]α-(methoxymethylene) benzene acetate, (Z,E) isomer 930 mg of the product of Example 7 were mixed together under an inert atmosphere with 5 ml of carbon tetrachloride and then 480 mg of bromine in solution in 2 ml of carbon tetrachloride were added. The mixture was heated for 4 hours at 60° C. and the mixture was poured into 50 ml of water and extracted with methylene chloride. The organic phase was dried and the solvent was evaporated off. The residue was chromatographed on silica (eluant: hexane - isopropyl ether 7–3) to obtain 330 mg of the expected product melting at 154.2° C.

EXAMPLE 21

Methyl 2-[2-[3-ethynylohenyl)-2-fluoroethenyl]-α-(methoxymethylene) benzene acetate, (Z,E) isomer

STEP A

Methyl 2-2-fluoro-2-[3-[2-(trimethylsilylethynyl)-phenyl]-ethenyl]-α-(methoxymethylene) benzene acetate, (Z,E) isomer 2.3 ml of trimethylsilylacetylene were added over 4 to 5 minutes to a mixture of 1.96 g of the product of Example 19, 14 ml of acetonitrile, 20 ml of triethylamine, 0.54 g of palladium at 10% on activated charcoal, 48 mg of coppr iodide and 0.22 g of triphenylphosphine. The mixture was heated for 20 hours at 80° C. in a closed vessel, then cooled to 5° C. and filtered. The filtrate was poured into water and was extracted with methylene chloride, washed with water, dried and the solvent was evaporated off. After chromatography on silica (eluant: hexane - ethyl acetate 8–2) 0.95 g of the expected product melting at 119° C. were obtained.

STEP B

Methyl 2-[2-[3-ethynylphenyl)-2-fluoroethenyl]-α-(methoxymethylene) benzene acetate, (Z,E) isomer A solution of 1.6 ml of tert.-butyl ammonium fluoride in a 1M solution in tetrahydrofuran was introduced at −70° C. into a solution of 0.63 g of the product of Step A and 20 ml of tetrahydrofuran. The reaction mixture was stirred for 3 hours at −70° C. and was then poured into an aqueous solution of potassium dihydrogen phosphate cooled to 0°/+5° C. The mixture was stirred for 15 minutes and extracted with methylene chloride, washed with water and dried. The solvent was evaporated and after chromatography on silica (eluant: hexane - ethyl acetate 8–2) and crystallization from pentane, 0.35 g of the expected product were obtained which melted at 103° C.

EXAMPLE 22

Methyl [4-(3,3-dimethyl-1-butynyl)-3-(trifluoromethyl)-phenyl]-2-fluoroethenyl-α-(methoxymethylene) benzene acetate, (Z,E) isomer 0.92 g of the product (Z,E isomer) of Example 1, 7 ml of acetonitrile, 9 ml of triethylamine, 0.2 g of palladium activated charcoal, 0.1 g of triphenylphosphine, 0.02 g of copper iodide and 1 ml of tert.-butyl acetylene were heated at 80° C. for 48 hours in a closed vessel. After cooling, filtration took place and the solvent was evaporated off. The residue was chromatographed on silica (eluant: methylene chloride) to obtain 0.5 g of the expected product (Z,E) isomer melting at 124° C.

EXAMPLE 23

Methyl 2-[2-(3-ethenylphenyl)-2-fluoroethenyl]-α-(methoxymethylene) benzene acetate, (Z,E) isomer 2.35 g of the product of Example 19, 30 ml of toluene, 0.28 g of palladium triphenylphosphine and 2 ml of vinyltributyltin were refluxed at 110° C. with stirring for 16 hours at this temperature. After cooling to 20° to 25° C., the solvent was evaporated off to obtain 5 g of crude product which was chromatographed on silica (eluant: isopropyl ether - hexane 65 to 35) to obtain 1.29 g of the expected product melting at 86° C.

EXAMPLE 24

Methyl 2-[2-[3-(3-trifluoromethylphenyl)-phenyl]-2-fluoroethenyl -α-(methoxymethylene) benzene acetate, (Z,E) isomer

STEP A

Methyl 2-[2-(3-tributyl-stannanephenyl)-2-fluoroethenyl]-α-(methoxymethylene) benzene acetate Using the procedure of Example 21, 5.9 g of the product of Example 19, 90 ml of toluene, 9.8 ml of hexabutyl distannane and 0.86 g of palladium triphenylphosphine were reacted by heating for 8 hours at 110° C. After chromatographing on silica (eluant: methylene chloride - hexane 6-4), 9 g of the expected product were obtained.

STEP B

Methyl 2-[2-[3-(3-trifluoromethylphenyl)-phenyl]-2-fluoroethenyl]-α-(methoxymethylene) benzene acetate, (Z,E) isomer 3.5 g of the product of Step A, 35 ml of 3-(trifluoromethyl)-iodobenzene and 0.2 g of palladium bis(-triphenylphosphine) chloride were heated to 110° C. for 16 hours. The reaction medium was cooled to ambient temperature, filtered and the solvent was evaporated. The residue was chromatographed on silica (eluant: methylene chloride - hexane 65–35) to obtain 1.4 g of the expected product melting at 119.5° C.

EXAMPLE 25

Methyl 2-[2-[5-bromo-4-(4-fluorophenyl)-2-thiazolyl]-2-fluoroethenyl]-α-(methoxymethylene) benzene acetate, (Z,E) isomer and (E,E) isomer Using the procedure of Example 1, 11.36 g of 2-formyl-α-(methoxymethylene) benzene acetate, 22 g of diethyl [[5-bromo-4-(4-fluorophenyl)-2-thiazolyl]-fluoromethyl phosphonate (Preparation 19) and 6.5 g of potassium tert.-butylate were reacted to obtain 26.6 g of crude product which was chromatographed on silica (eluant: hexane - isopropyl ether 1–1) to obtain 920 mg of the (Z,E) isomer melting at 189° C., and 20 mg of the (E,E) isomer melting at 133° C.

EXAMPLE 26

Methyl 2-[2-fluoro-2-[3-[4-(trifluoromethoxy)-phenyl]-1,2,4-oxadiazol-5-yl]-ethenyl]-α-(methoxymethylene) benzene acetate, (Z,E) isomer 465 mg of the product of Example 15 (E,E isomer) dissolved in 5 ml of carbon tetrachloride was placed under luminous radiation (250 watts) and then 0.1 ml of a 5% solution of bromine in carbon tetrachloride was added. At the end of the reaction, the solvent was evaporated and the residue was treated with pentane to obtain 400 mg of the expected product Z,E isomer melting at 137° C.

EXAMPLE 27

Methyl 2-[2-[3-(trifluoromethyl)-phenyl-2-chloroethenyl]-α-(methoxymethylene) benzene acetate, (Z,E) isomer and (E,E) isomer A solution of 2.48 g of diethyl [3-trifluoromethyl)-phenyl]-chloromethyl]-phosphonate (Preparation 20), 1.65 g of methyl-2-formyl-α-(methoxymethylene)benzene acetate (Preparation 1) in 20 ml of tetrahydrofuran was cooled to −70° to −75° C. and then 0.95 g of potassium tert.-butylate dissolved in 10 ml of tetrahydrofuran were added over 45 minutes. The mixture was stirred for 1 hour at −65° to −70° C. and then the mixture was poured into a water +2N hydrochloric acid mixture cooled to 0° to −5° C. The mixture was stirred for 15 minutes at pH 3–4 and extraction was carried out with methylene chloride. The organic extracts were washed with water until neutral, dried and the solvent was evaporated. The residue was chromatographed on silica (eluant: hexane ethyl acetate 85–15) to obtain 1.48 g of the (E,E) isomer and 0.92 g of the (Z,E) isomer after crystallization from and washing with pentane.

EXAMPLE 28

Methyl 2-[2-[3-(trifluoromethyl)-phenyl-2-bromoethenyl]-α-(methoxymethylene) benzene acetate, (E,E) isomer Using the procedure of Example 27, 2.81 g of diethyl [3-(trifluoromethyl)-phenyl]-2-bromomethyl]-phosphonate (Preparation 21) and 1.65 g of methyl 2-formyl-α-(methoxymethylene) benzene acetate (Preparation 1) were reacted to obtain 1.35 g of the expected product.

EXAMPLE 29

Methyl 2-[2-[3-(trifluoromethyl)-phenyl-2-bromoethenyl]-α-(methoxymethylene) benzene acetate, (Z,E) isomer 0.23 ml of a 5% solution of bromine in carbon tetrachloride were added to 1 g of the product of Example 28 (E,E, isomer) in 15 ml of carbon tetrabromide and the reaction medium was placed under luminous radiation (300 watts) for 2 hours. After evaporating the solvent, 1.2 g of crude product were purified by chromatography on silica (eluant: hexane - ethyl acetate 8–2) to obtain 0.42 g of the expected product melting at 94° C.

Using the procedure of the preceding examples, the following product was prepared.

EXAMPLE 30

Methyl 2-[2-fluoro-2-[3-phenyl 1,2,4-oxadiazol-5-yl]-ethenyl] -α-(methoxymethylene) benzene acetate, (Z,E) isomer melting at 121° C.

PREPARATION 1

Methyl 2-formyl-α-(methoxymethylene) benzene acetate 50.7 g of a solution of methyl 2-bromoethyl-α-(methoxymethylene) benzene acetate (prepared by the process of EP 203,606) and 100 ml of methylene chloride were introduced at 0° C. into a mixture of 55 g of anhydrous trimethylamine N-oxide, 350 ml of dimethylsulfoxide and 160 ml of methylene chloride. The reaction mixture was stirred for 4 hours at approx. 20° to 25° C. and then was poured into a water and ice mixture. After decanting, extracting with methylene chloride, drying and bringing to dryness, the product obtained was chromatographed on silica (eluant: hexane - ethyl acetate (8–2)) to obtain 17.5 g of the desired product melting at 81° C.

PREPARATION 2

Diethyl [[4-bromo-3-trifluoromethyl-phenyl]-fluoromethyl phosphonate

STEP A 4-bromo-3-trifluoromethyl-benzaldehyde a) Preparation of 4-bromo-3-trifluoromethyl-benzene diazonium chloride 60 g of 4-bromo-3-trifluoromethyl-aniline were introduced into 60 ml of water and then 57 ml of concentrated hydrochloric acid were introduced. The suspension was allowed to return to 20° C. and ice was added. A solution of 17.5 g of sodium nitrite and 25 ml of water was added at 0°±5° C. and the mixture was stirred at 0°±5° C., for 15 minutes. A solution of 25 g of hydrated sodium acetate and 35 ml of water was added. An aqueous solution of formaldehyde-oxime at 10% prepared in the following manner was added at 10° C. to 15° C. to this solution:

b) Preparation of an aqueous solution of formaldehyde-oxime at 10%.

26.3 g of hydroxylamine hydrochloride were introduced into 170 ml of distilled water and 28.75 g of formaldehyde at 40% were added. The mixture was heated to 40° C. and 51 g of hydrated sodium acetate were added. The mixture was refluxed for 15 minutes, then left to stand for 16 hours. 6.5 g of copper sulfate and 1 g of sodium sulfate were added and after cooling to 15° C., a solution of 160 g of sodium acetate and 300 ml of distilled water was introduced.

The solution of the diazonium salt obtained in a) was added at 10° to 15° C. to the solution of b) followed by stirring for 1 hour at 15° C. 230 ml of concentrated hydrochloric acid were added and the mixture was refluxed for 2 hours. After cooling and extracting 6 times with 400 ml of ethyl ether, the organic solution was washed with a saturated solution of sodium bicarbonate and with water saturated with sodium chloride, then dried, filtered and concentrated to dryness to obtain 66.3 g of product which was chromatographed on silica (eluant: hexane - ethyl acetate (95–5)) to obtain 11.15 g of the desired product.

| IR Spectrum CHCl₃ | |
| --- | --- |
| C=0 | 1707 cm⁻¹ |
| CHO | 2735 cm⁻¹ |
| Aromatics | 1600-1580-1570-1470 cm⁻¹ |

STEP B
Diethyl [4-bromo-3-trifluoromethyl-hydroxymethyl]-phosphonate 12.65 g of 4-bromo-3-trifluoromethyl-benzaldehyde of Step A were introduced at about 60° C. into a mixture of 6.5 ml of diethylphosphite and 0.5 ml of triethylamine. The mixture was stirred for 1 hour at 70° C. followed by cooling to 40° C. Then, 100 ml of toluene were added and after washing with an aqueous solution of 1N hydrochloric acid, then with water, drying and evaporating to dryness, 17.4 g of product melting at 88° C. were obtained.

STEP C

Diethyl [[4-bromo-3-trifluoromethyl-phenyl]-fluoromethyl] phosphonate 2.5 ml of diethylamino sulfide trifluoride were added at 0° C. to a mixture of 7.82 g of the product of Step B dissolved in 50 ml of methylene chloride. The reaction mixture was held at approx. 20° to 25° C. for 1 hour and then was poured into a saturated aqueous solution of sodium bicarbonate, followed by decanting, extracting with methylene chloride, drying and bringing to dryness. The product was chromatographed and eluted with a methylene chloride - tetrahydrofuran (98-2) mixture to obtain 5.7 g of the desired product with a Rf=0.2.

PREPARATION 3

Diethyl [[2-(3,4-dichlorophenyl)-4-thiazolyl]-fluoromethyl]-phosphonate

STEP A

Diethyl [[2-(3,4-dichlorophenyl)-4-thiazolyl]-hydroxymethyl] phosphonate

A mixture of 3.9 ml of diethylphosphite and 0.3 ml of triethylamine was heated to 60° C. and 12.65 g of the product 2-[2-(3,4-dichlorophenyl)-4-formyl thiazole (described in EP 402,246) were introduced. After heating to 160° C., the temperature is allowed to return to 110° C. and then, the mixture was heated at 110° C. for 4 hours, followed by allowing the temperature to return to 20° to 25° C. The product was poured into 1 liter of methylene chloride and the reaction medium was poured into 100 ml of a normal solution of hydrochloric acid. The chloromethylene phase was decanted, dried and evaporated to dryness. The product was washed with isopropyl ether and dried under reduced pressure to obtain 5.9 g of the desired product melting at 155° C.

STEP B

Diethyl [2-[2-(3,4-dichlorophenyl)-4-thiazolyl]-fluoromethyl]-phosphonate

Using the procedure of Preparation 2, the product of Step A was reacted to obtain 2.4 g of the desired product with a Rf=0.25 (eluant: methylene chloride - isopropyl ether (30–10)).

PREPARATION 4

Diethyl [2-[4-trifluoromethoxyl]-4-thiazolyl]-fluoromethyl]-phosphonate

STEP A

Diethyl 2-[4-trifluoromethoxy)-4-thiazolyl]-hydroxy methyl]-phosphonate 2.74 g of 2-[2-[4-trifluoromethoxy)-phenyl]-4-formyl thiazole of EP 402,246 were added at 70° C. to a solution of 1.3 ml of diethylphosphite and 0.1 ml of triethylamine and the mixture was allowed to cool to 40° C. 15 ml of toluene were added and after washing with a normal solution of hydrochloric acid, then with water, the aqueous phases were extracted with methylene chloride. The combined organic phases were dried and after filtering and rinsing, the solvent was eliminated to obtain 2.87 g of the desired product (isolated from pentane) with a Rf=0.08 (methylene chloride - tetrahydrofuran (9–1).

STEP B

Diethyl [[2-[4-trifluoromethoxy-4-thiazolyl]-fluoromethyl] phosphonate 2 ml of diethylamino sulfide trifluoride at 95% were added at −5° C. to a solution of 6.1 g of diethyl [[2-[4-trifluoromethoxy-4thiazolyl]-hydroxy methyl]-phosphanate and the reaction mixture was poured into a saturated aqueous solution of sodium bicarbonate and extracted with methylene chloride. The combined organic phases were dried and the solvent was evaporated to obtain 6.42 g of a product which was chromatographed on silica eluting with a methylene chloride - isopropyl ether (9-1) mixture to obtain 2.3 g of the desired product.

PREPARATION 5

Diethyl [fluoro-[4-phenyl-2-thiazolyl]-methyl]phosphonate

STEP A

Diethyl ester of [(aminocarbonyl)-fluoromethyl]-phosphonic acid 700 ml of 22°Be ammonium hydroxide were introduced at 5° to 10° C. under a current of nitrogen with stirring into 664 g of methyl (diethoxy-phosphinyl) fluoro acetate and the reaction mixture was stirred for 3 hours. The excess ammonium hydroxide was distilled under reduced pressure and the reaction medium was saturated with sodium chloride. Extraction took place with methylene chloride, followed by washing with a saturated solution of sodium chloride. The chloromethylene phase was dried, followed by filtering and evaporating to dryness under reduced pressure to obtain 646 g of the desired crude product which was dissolved in 1 liter of methylene chloride. Distillation took place under reduced pressure at constant volume by replacing the methylene chloride with isopropyl ether, followed by separating, washing and drying to obtain 551.4 g of the desired product.

STEP B

Diethyl [(2-amino-1-fluoro-2-thioxo)-ethyl]-phosphonate

A suspension of 57.9 g of diethyl [2-amino-1-fluoro-2-oxo]ethyl]-phosphonate of Step A, 580 ml of tetrahydrofuran and 16 g of phosphorous pentasulfide was stirred for 5 hours at ambient temperature. After filtering, the solvent was evaporated to obtain 84.55 g of product which was chromatographed (eluant: acetone - cyclohexane (1-1)) to obtain 26.6 g of the desired product.

STEP C

Diethyl [fluoro-[4-phenyl-2-thiazolyl]-methyl]-phosphonate

A mixture of 2.3 g of the product of Step B, 30 ml of methanol and 2 g of -bromo acetophenone was refluxed for 90 minutes. The mixture was allowed to cool and was then poured into a water - ethyl acetate (100 ml to 50 ml) mixture. The reaction medium was neutralized, followed by decanting and extracting with ethyl acetate. After washing with water, drying and evaporating, 3.18 g of product were obtained which was chromatographed on silica (eluant: methylene chloride - tetrahydrofuran (98-2)) to obtain 2.47 g of the desired product.

PREPARATION 6

Diethyl [fluoro-[4-(1-methylethyl)-2-thiazolyl]-methyl-phosphonate

Using the procedure of Step C, 1-bromo-3-methyl-2-butanone was reacted to obtain 4.13 g of the desired product with a Rf=0.23 (methylene chloride - tetrahydrofuran (95-5)).

PREPARATION 7

Diethyl [[4-(3,4-dichlorophenyl)-2-thiazolyl]-fluoromethyl phosphonate

STEP A

3', 4'-dichloro-bromoacetoohenone 55.85 g of cupric bromide, 23.75 g of 3', 4'-dichloroacetophenone in 125 ml of chloroform and 125 ml of ethyl acetate containing traces of hydrobromic acid were stirred for 3 hours at reflux. After filtering, the filtrate was treated with 30 g of activated charcoal, filtered again and concentrated under reduced pressure. The residue was taken up in 40 ml of ethyl ether to obtain 21.3 g of the desired product melting at 52° C. which was used as is for the following step.

STEP B

Diethyl [[4-(3,4-dichlorophenyl)-2-thiazolyl]-fluoromethyl]-phosphonate

A mixture of 2.3 g of the product of Preparation 5, Step A or diethyl [(2-amino-1-fluoro-2-thioxo)-ethyl]-phosphonate, 30 ml of methanol and 3.4 of 3', 4'-dichloro-α-bromo acetophenone of Step A was refluxed for 2 hours 45 minutes. Vigorous stirring and neutralization took place, followed by decanting, extracting with ethyl acetate, washing with water, drying and evaporating the solvent to obtain 3.64 g of crude product which was chromatographed and eluted with a methylene chloride - tetrahydrofuran (98-2) mixture to obtain 2.8 g of the desired product with a Rf=0.3.

PREPARATION 8

Diethyl [fluoro-[2-(trifluoromethyl)-4-thiazolyl]-methyl] phosphonate

Using the procedure of Preparation 2, Steps B and C, the appropriate aldehyde was reacted to obtain the expected product with a Rf=0.2 (methylene chloride - tetrahydrofuran 98-2).

PREPARATION 9

Diethyl 4-[[1,1'-biphenyl]-4-yl]-2-thiazolyl]-fluoromethyl]-phosphonate

A mixture of 3.4 g of the product of Step B of Preparation 5, 45 ml of methanol and 4.1 g of 1-[(1,1'-biphenyl)-4-yl]-2-bromoethanone was refluxed for 7 hours and after cooling, the mixture was poured into a water - ethyl acetate (200 ml to 100 ml) mixture. The reaction medium was neutralized, decanted and extracted with ethyl acetate. After washing with water, drying and evaporating, 6.1 g of crude product were cbtained which was crystallized from pentane to obtain 5 g of the expected product melting at 91.2° C.

PREPARATION 10

Diethyl [[4-(4-chlorophenyl)-2-thiazolyl]-fluoromethyl]-phosphonate

Using the procedure of Step C of Preparation 5, 3.44 g of the phosphonate of Step B and 3.5 g of 2-bromo-4'-chloroacetophenone were reacted to obtain 2.83 g of the expected product with a Rf=0.17 (methylene chloride - tetrahydrofuran 98-2).

PREPARATION 11

Diethyl [[4-(4-bromophenyl)-2-thiazolyl]-fluoromethyl]-phosphonate

Using the procedure of Step C of Preparation 5, 3.44 g of the phosphonate of Step B and 4.17 g of 2-bromo-4'-bromoacetophenone were reacted to obtain 4.6 g of

PREPARATION 12

Diethyl [fluoro-[4-(trifluoromethyl-2-thiazolyl]-methyl]-phosphonate 6.9 g of the phosphonate of Step B of Preparation 5 and 5.8 g of 1-bromo-3,3,3-trifluoroacetophenone were mixed together and the mixture was diluted with 20 ml of methylene chloride, washed with water and dried. The solvent was evaporated and the residue was chromatographed on silica (eluant: methylene chloride - tetrahydrofuran 98–2) to obtain 2.2 g of the expected product with a Rf=0.05 (hexane - ethyl acetate 7–3).

PREPARATION 13

Diethyl [2'-ethyl-(2, 4'-bithiazole)-4-yl]-fluoromethyl phosphonate

Using the procedure of Preparation 2, Steps B and C, the appropriate aldehyde was reacted to obtain the expected product with a Rf=0.05 (hexane - ethyl acetate 7–3).

PREPARATION 14

Diethyl [fluoro-[2-(2-pyridinyl)-4-thiazolyl]-methyl]-phosphonate

Using the procedure of Preparation 2, Steps B and C, the appropriate aldehyde was reacted to obtain the expected product with a Rf=0.47 (methylene chloride - tetrahydrofuran 85–15).

PREPARATION 15

Diethyl [fluoro-[3-[4-trifluoromethoxy-phenyl]-1,2,4-oxadiazol-5yl]-methyl]-phosphonate

STEP A

N-hydroxy 4-trifluoromethoxy-benzene carboximidamine 3.8 ml of triethylamine were added over 5 minutes to 2.05 g of hydroxylamine hydrochloride in 30 ml of methanol and the mixture was stirred for 30 minutes at ambient temperature. Then, 5 g of 4-trifluoromethoxy benzonitrile in 10 ml of methanol were added and the mixture was refluxed for 50 minutes. After cooling, the solvent was evaporated and the residue was taken up in methylene chloride, washed with water and dried. The solvent was eliminated under reduced pressure to obtain 5 g of the expected product melting at 111° C.

STEP B

Diethyl [fluoro-[3-[4-trifluoromethoxy-phenyl]-1,2,4-oxadiazol-5-yl]-methyl]-phosphonate 4.93 g of the oxime of Step A and 4.8 g of (diethoxy phosphoryl) fluoroacetic acid in 90 ml of methylene chloride were mixed together at ambient temperature and 5.8 g of dicyclohexycarbodiimide and 140 mg of dimethylaminopyridine in 20 ml of methylene chloride were added dropwise. The urea was filtered and the solvent was evaporated to obtain 11.45 g of product to which 30 ml of toluene were added. The mixture was refluxed for 1 hour and after cooling, the solvent was evaporated off. The residue was chromatogrphed on silica (eluant: hexane - tetrahydrofuran 7–3) to obtain 6.45 g of the expected phosphonate.

PREPARATION 16

Diethyl [fluoro-[3-(trifluoromethyl)-phenyl]-methyl]-phosphonate

Using the procedure of Preparation 2, Steps B and C, 3-trifluoromethyl benzaldehyde was reacted to obtain the expected product with a Rf=0.17 (methylene chloride - tetrahydrofuran 98–2).

PREPARATION 17

Diethyl [fluoro-[4-(4-nitrophenyl)-2-thiazolyl]-methyl]-phosphonate

Using the procedure of Preparation 9, 5.5 g of diethyl [(2-amino-1-fluoro-2-thioxo)-ethyl]-phosphonate and 4.93 g of 2-bromo-3'-nitro-acetophenone were reacted to obtain 9.46 g of crude product which was chromatographed on silica (eluant: methylene chloride - isopropyl ether 85–15) to obtain 4.22 g of the expected product melting at 100° C.

PREPARATION 18

Diethyl[fluoro-[4-(fluorophenyl)-2-thiazolyl]-methyl]-phosphonate

Using the procedure of Preparation 9, 36.6 g of diethyl [(2-amino-1-fluoro-2-thioxo)-ethyl]-phosphonate and 31.8 g of 2-bromo-4'-fluoro-acetophenone were reacted to obtain 56.8 g of crude product which was chromatographed on silica (eluant: methylene chloride - tetrahydrofuran 98–2) to obtain 28.58 g of the expected product melting at 100° C.

PREPARATION 19

Diethyl [[5-bromo-4-(4-fluorophenyl)-2-thiazolyl]-fluoromethyl phosohonate

STEP A

Diethyl [(2-amino-1-fluoro-2-thioxo)-ethyl]-phosphonate 16 g of phosphorous pentasulfide were added to 57.9 g of diethyl [(2-amino-1-fluoro-2-oxo)-ethyl] phosphonate in 500 ml of tetrahydrofuran and the mixture was stirred for 5 hours at ambient temperature. After filtering, the solvent was evaporated off and the residue was chromatographed on silica (eluant: chloroform - acetone - cyclohexane 1-1-1) to obtain 26.6 g of the expected product melting at 52.6° C.

STEP B

Diethyl [4(4-fluorophenyl)-2-thiazolyl]-fluoromethyl-phosphonate 33.6 g of the phosphonate of Step A, 500 ml of ethanol and 31.8 g of 2-bromo-4-fluoro-acetophenone were refluxed for 30 minutes and after cooling to ambient temperature, the reaction mixture was poured into 500 ml of water and extracted with ethyl acetate. The solvent was evaporated and the residue was chromatographed on silica (eluant: methylene chloride tetrahydrofuran 98–2) to obtain 28.58 g of the expected product.

STEP C

Diethyl [[5-bromo-4-(4-fluorophenyl)-2-thiazolyl]-fluoromethyl phosphonate 21.7 g of the phosphonate of Step B, 250 ml of acetonitrile and 14.5 g of N-bromo-succinimide were refluxed for one hour. After cooling, the solvent was evaporated off and the residue was chromatographed on silica (eluant: methylene chloride - tetrahydrofuran 98-2) to obtain 24 g of the expected product.

PREPARATION 20

Diethyl 3-trifluoromethyl-phenyl-chloromethyl]-phosohonate

Using the procedure of Preparation 2 Step B, 3-trifluoromethyl benzaldehyde was reacted to obtain diethyl [3-trifluoromethylhydroxymethyl] phosphonate. 1.6 ml of pyridine and then over 20 minutes 1.6 ml of thionyl chloride were added to 6.26 g of this phosphonate in 60 ml of methylene chloride and the mixture was stirred for 1 hour at ambient temperature, followed by heating to 40° C. for 28 hours, cooling to 20° to 25° C., washing with an aqueous solution of sodium bicarbonate, then with water, drying and evaporating the solvent to obtain 6.4 g of crude product. The residue was purified by chromatogrphy on silica (eluant: hexane - ethyl acetate 5-5) to obtain 5.15 g of the expected product.

PREPARATION 21

Diethyl [3-trifluoromethyl-phenyl-bromomethyl]-phosphonate 6.26 g of diethyl [3-trifluoromethyl-hydroxymethyl]-phosphonate in 60 ml of methylene chloride wre cooled to 0° to +5° C. and 9.95 g of tetrabromo-carbon were added over 10 minutes. The temperature was allowed to rise to +7° to +10° C. and 7.9 g of triphenylphosphine were added. The temperature was allowed to return to ambient temperature and the mixture was stirred for 48 hours. After filtering, the filtrate was poured into a saturated aqueous solution of sodium bicarbonate. The mixture was stirred for 20 minutes, followed by extraction with methylene chloride. The organic phase was washed with water, dried and the solvent was evaporated to obtain 18 g of crude product. The product was taken up in a hexane - ethyl acetate 5-5 mixture, filtered, and the solvent was evaporated. The residue was chromatographed on silica (eluant: hexane - ethyl acetate 5-5) to obtain 5.55 g of the expected product.

EXAMPLES OF INSECTICIDE COMPOSITIONS

Example 31

Preparation of a Soluble Concentrate

A homogeneous mixture of the following was prepared:

| Product of Example 1 (Z,E isomer) | 0.25 g |
|---|---|
| Tween 80 | 0.25 g |
| Topanol A | 0.1 g |
| Water | 98.4 g |

Example 32

Preparation of an Emulsifiable Concentrate

The following were intimately mixed together:

| Product of Example 7 (Z,E isomer) | 0.015 g |
|---|---|
| Topanol A | 0.1 g |
| Tween 80 | 3.5 g |
| Xylene | 95.885 g |

Study of the Activity of the compounds of the Invention a) Study of the Activity on *Aphis craccivora*

Bean plants were treated by dipping the leaves in a water-acetone solution of active ingredient (50% acetone, 50% water) and then dried under a ventilated hood. The leaves were then infested with 20 adult *Aphis craccivora* females per leaf and kept at 22° C. under a luminous ceiling. Mortality checks were carried out after 48 hours.

Results

With a dose of 10 ppm, the products of Examples 2, 3, 4, 7, 8, 10, 11, 12, 14, 16, 17, 18, 20, 21, 22, 24, 25, 26 and 30 showed an effectiveness of $\geq 75\%$.

b) Study of the Effect on Sopdoptera Littoralis Larvae by Contact and Ingestion

Step L3 larvae of *Spodoptera littoralis* were used and the operation took place at 22° C. in 50% relative humidity conditions. Petri dishes were used containing a damp circle of filter paper and two bean leaves treated with a water-acetone solution (50-50) containing the product to be tested were placed in each dish. The number of dead larvae was counted after 7 days.

Results

With a dose of 10 ppm, the products of Examples 2, 4, 7, 8, 9, 10, 11, 15, 16, 17, 18, 20, 25, 26 and 30 had an effectiveness of $\geq 75\%$.

c) Study of the Effect on *Phaedon cochleariae*

The operation took place at 22° C. at 50% relative humidity conditions. Petri dishes were used containing a damp circle of filter paper and two disks of Chinese cabbage leaf treated with a water-acetone solution (50-50) containing the product to be tested. The number of dead insects was counted after one week.

Results

With a dose of 10 ppm, the products of Examples 10, 18, 25 and 26 had an effectiveness of $\geq 75\%$.

d) Study of the Effect on *Tetranychus urticae*

Haricot bean plants were used with 2 leaves infested with 30 Tetranychus urticae females per leaf and put under a ventilated hood under a luminous ceiling with constant illumination. The plants were treated with a Fisher gun using 4 ml of toxic solution per plant of an equal volume mixture of water and acetone. The leaves were left to dry for 30 minutes and then infestation proceeded. Mortality checks were carried out after 3 days.

Results

With a dose of 10 ppm, the products of Examples 1, 2, 3, 4, 6, 8, 10, 11, 12, 13, 15, 16, 18, 20, 22, 25, 26 and 30 had an effectivness of $\geq 75\%$.

Various modifications of the products and method of the invention may be made without departing from the spirit or scope thereof and it is to be understood that the invention is intended to be limited only as defined in the appended claims.

What we claim is:

1. All possible stereoisomer forms and mixtures of a compound of the formula $$\underset{R_1}{\overset{X}{\diagdown}}C \underset{\Delta_1}{\overset{}{=}}CH \diagup \overset{\displaystyle \bigcirc}{\underset{R_2 \diagdown O \diagup \overset{}{\underset{\Delta_2}{=}} \diagdown CO_2R_3}{}} \qquad I$$

wherein X is a halogen, $R_2$ and $R_3$ are individually selected from the group consisting of alkyl and cycloalkyl of up to 8 carbon atoms optionally substituted with at least one halogen, $R_1$ is selected from the group consisting of alkyl, alkenyl, alkynyl and cycloalkyl of up to 12 carbon atoms optionally substituted with at least one halogen, hydrocarbyl aryl and heterocycle selected from the group consisting of pyridyl, pyrimidyl, pyridazinyl, oxazolyl, thiazolyl, isoxazolyl, isothiazolyl, (1,3,4)-oxadiazolyl, (1,2,4)-oxadiazolyl, thiadiazolyl and triazolyl optionally substituted with at least one member of the group consisting of halogen, alkyl, alkenyl, alkynyl and cycloalkyl of up to 8 carbon atoms optionally substituted with at least one member of the group consisting of $-NO_2$, $-NH_2$, $-CN$, $-OR'$, $-SR''$, $-SOR''$, $-SO_2R''$, $-NR'''_2$, $-Ar$, $-OAr_1$ and $SAr_2$, R', R'' and R''' are individually selected from the group consisting of alkyl, alkenyl alkynyl and cycloalkyl of up to 12 carbon atoms optionally substituted by at least one halogen, Ar, $Ar_1$ and $Ar_2$ are hydrocarbyl aryl of up to 14 carbon atoms or heteroaryl selected from the group consisting of pyridyl, pyrimidyl, pyridazinyl, oxazolyl, thiazolyl, isoxazolyl, isothiazolyl, (1,3,4) -oxadiazolyl, (1,2,4) -oxadiazolyl, thiadiazolyl and triazolyl optionally substituted with at least one member of the group consisting of halogen and alkyl, alkenyl, alkynyl and cycloalkyl of up to 8 carbon atoms optionally substituted by at least one member of the group consisting of $-NO_2$, $-NH_2$, $-CN$, $-OR'$, $-SR''$, $-SOR''$, $-SO_2R''$, $-NR'''_2$, R', R'' and R''' have the above definitions.

2. A compound of claim 1 wherein the double bond is of E geometry.

3. A compound of claim 1 wherein $R_2$ is methyl.

4. A compound of claim 1 wherein $R_3$ is methyl.

5. A compound of claim 1 wherein X is fluorine.

6. A compound of claim 1 wherein $R_1$ is phenyl optionally substituted by at least one member of the group consisting of halogen and $-CF_3$.

7. A compound of claim 1 wherein $R_1$ is thiazolyl optionally substituted by at least one member of the group consisting of halogen, alkyl, alkenyl, alkynyl and cycloalkyl of up to 8 carbon atoms optionally substituted with at least one member of the group consisting of $-NO_2$, $-NH_2$, $-CN$, $-OR'$, $-SR''$, $-SOR''$, $-SO_2R''$ and $-NH'''_2$, Ar, $Ar_1$ and $Ar_2$, with R', R'', R''', Ar, $Ar_1$ and $Ar_2$, defined as in claim 1.

8. A compound of claim 1 wherein $R_1$ is thiazolyl optionally substituted by at least one halogen or phenyl optionally substituted with at least one member of the group consisting of halogen, $-CF_3$ and $-OCF_3$.

9. A compound of claim 1 wherein $R_1$ is oxadiazolyl optionally substituted by at least one member of the group consisting of halogen, alkyl, alkenyl, alkynyl and cycloalkyl of up to 8 carbon atoms optionally substituted with at least one member of the group consisting of $-NO_2$, $-NH_2$, $-CN$, $-OR'$, $-SR''$, $-SOR''$, $-SO_2R''$ and $-NR'''_2$, Ar, $Ar_1$ and $Ar_2$, with R', R'', R''', Ar, $Ar_1$ and $Ar_2$, defined as in claim 1.

10. A compound of claim 1 wherein $R_1$ is oxadiazolyl substituted by phenyl optionally substituted with at least one member of the group consisting of halogen, $-CF_3$ and $-OCF_3$.

11. A compound of claim 1 selected from the group consisting of (E,E) methyl 2-[2-[4-(3,4-dichlorophenyl-2-thiazolyl]-2-fluoroethenyl-α-(methoxymethylene) benzene acetate, (Z,E) methyl 2-[2-fluoro-2-(4-phenyl-2-thiazolyl)-ethenyl]-α-(methoxymethylene) benzene acetate, (E,E) methyl 2-[2-[4-bromo-3-trifluoromethyl-phenyl-2-fluoroethenyl]-α-(methoxymethylene) benzene acetate, (E,Z) methyl 2-[2-[4-bromo-3-trifluoromethyl-phenyl]-2-fluoroethylenyl]-60 -(methoxymethylene) benzene acetate, (Z,E) methyl 2-[2-[4-(3,4-dichlorophenyl)-2-thiazolyl]-2-fluoroethenyl]-α-(methoxymethylene) benzene acetate, (Z,E) methyl 2-[2-fluoro-2-[4-thiazolyl-2-(4-trifluoromethoxy)phenyl]-ethenyl]-α-(methoxymethylene) benzene acetate, (Z,E) methyl 2-[2-[4-(4-fluorophenyl)-2-thiazolyl]-2-fluoroethenyl]-α-(methoxymethylene) benzene acetate, (Z,E) methyl 2-[2-[5-bromo-4-(3,4-dichlorophenyl)-2-thiazolyl]-2fluoroethenyl]-α-(methoxymethylene) benzene acetate, (Z,E) methyl 2-[2-[5-bromo-4-(4-fluorophenyl)-2-thiazolyl]-2-fluoroethenyl]-α-(methoxymethylene) benzene acetate, (Z,E) methyl 2-[2-fluoro-2-[3-[4-trifluoromethoxyphenyl]-1,2,4-oxadiazol-5-yl]-ethenyl]-α-(methoxymethylene) benzene acetate, (Z,E) methyl 2-[2-fluoro-2-[3-phenyl-1,2,4-oxadiazol-5-yl]-ethenyl]-α-(methoxymethylene) benzene acetate.

12. An insecticidal composition comprising an insecticidally effective amount of at least one compound of claim 1 and an inert carrier.

13. An acaricidal composition comprising an acaricidally effective amount of at least one compound of claim 1 and an inert carrier.

14. A nematocidal composition comprising a nematocidally effective amount of at least one compound of claim 1 and an inert carrier.

15. A method of combatting insects comprising contacting insects with an insecticidally effective amount of at least one compound of claim 1.

16. The method of claim 15 wherein the active compound is selected from the group consisting of (E,E) methyl 2-[2-[4-(3,4-dichlorophenyl-2-thiazolyl]-2-fluoroethenyl-α-(methoxymethylene) benzene acetate, Z,E) methyl 2-[2-fluoro-2-(4-phenyl-2-thiazolyl)-ethenyl]-α-(methoxymethylene) benzene acetate, (E,E) methyl 2-[2-[4-bromo-3-trifluoromethyl-phenyl-2-fluoroethenyl]-α-(methoxymethylene) benzene acetate, (E,Z) methyl 2-[2-[4-bromo-3-trifluoromethyl-phenyl]-2-fluoroethenyl-α-(methoxymethylene) benzene acetate, (Z,E) methyl 2-[2-[4-(3,4-dichlorophenyl)-2-thiazolyl]-2-fluoroethenyl]-α-(methoxymethylene) benzene acetate, (Z,E) methyl 2-[2-fluoro-2-[4-thiazolyl-2-(4-trifluoromethoxy)phenyl]-ethenyl]-α-(methoxymethylene) benzene acetate, (Z,E) methyl 2-[2-[4-(4-fluorophenyl)-2-thiazolyl]-2-fluoroethenyl]-α-(methoxymethylene) benzene acetate, (Z,E) methyl 2-[2-[5-bromo-4-(3,4-dichlorophenyl)-2-thiazolyl]-2fluoroethenyl]-α-(methoxymethylene) benzene acetate, (Z,E) methyl 2-[2-[5-bromo-4-(4-fluorophenyl)-2-thiazolyl]-2fluoroethenyl]-α-(methoxymethylene) benzene acetate, (Z,E) methyl 2-[2-fluoro-2-[3-[4-trifluoromethoxyphenyl]-1,2,4-oxadiazol-5-yl]-ethenyl]-α-(methoxymethylene) benzene acetate, (Z,E) methyl 2-[2-fluoro-2-[3-phenyl-1,2,4-oxadiazol-5-yl]-ethenyl]-α-(methoxymethylene) benzene acetate.

* * * * *